United States Patent [19]

Lerch

[11] Patent Number: 5,520,701
[45] Date of Patent: May 28, 1996

[54] SET FOR THE TREATMENT OF VASCULAR DEFORMATIONS

[76] Inventor: Karl-Dieter Lerch, Nordstrasse 16, D-58452 Witten, Germany

[21] Appl. No.: 260,018

[22] Filed: Jun. 15, 1994

[30] Foreign Application Priority Data

Jun. 16, 1993 [DE] Germany .................. 43 19 829.5

[51] Int. Cl.⁶ .................................. A61B 17/00
[52] U.S. Cl. .................. 606/142; 606/139; 606/151; 227/901; 227/902
[58] Field of Search ................. 606/142, 143, 606/139, 151, 157, 158, 221; 227/901, 902; 128/843

[56] References Cited

U.S. PATENT DOCUMENTS

| 3,518,993 | 7/1970 | Blake ........................... 606/142 |
| 4,458,682 | 7/1984 | Cerwin ......................... 606/158 |
| 5,100,418 | 3/1992 | Yoon et al. ................... 606/139 |
| 5,174,276 | 12/1992 | Crockard .................... 606/142 |
| 5,201,746 | 4/1993 | Shichman .................... 606/151 |
| 5,342,373 | 8/1994 | Stefanchik et al. ......... 606/142 |

FOREIGN PATENT DOCUMENTS

50-208020  8/1993  Japan ........................ 606/142

*Primary Examiner*—Stephen C. Pellegrino
*Assistant Examiner*—Jeffrey A. Schmidt
*Attorney, Agent, or Firm*—Max Fogiel

[57] ABSTRACT

In order to destroy vascular deformations in the human body, a clamp is provided which is made from titanium. The clamp is expanded in the relieved state and is transferable into the clamping position by a clamping ring, which is displaceable along the clamp in the attached state. The clamp is introduced into the body by a probe, which has a tubular casing and a positioning bar guided therein. The clamp is transferred into the region of the deformation and applied at the application location as a result of the clamping ring being transferred into the clamping position. The transfer is caused by a relative movement between tubular casing and positioning bar. The probe is then released from the positioned clamp.

9 Claims, 4 Drawing Sheets

SET FOR THE TREATMENT OF VASCULAR DEFORMATIONS

BACKGROUND OF THE INVENTION

The invention relates to a set for the treatment of vascular deformations. Such a set can be found in WO 90/05491.

To eliminate vascular deformations in the brain, such as angiomas and aneurysms, so-called aneurysma clips have been used for some time, such clips being made from an austenitic steel alloy of implant quality and having arms which assume their closed position, i.e. their clamping position, by the action of a spring which is associated with the clip. These clips are attached to the deformation by means of a pincer-like positioning tool, with which the arms are expanded in opposition to the spring forming a component part of the clip, the arms of the clip resuming their closed position, i.e. their clamping position, at the deformation by the action of the spring, which acts on said arms, when the positioning tool is released, so as to destroy the deformation. However, clips made from a steel alloy are not totally resistant to corrosion; rather, positioned clips release toxic corrosion products, that is to say their bio-compatibility is limited. A compatibility, which is at least limited, then also exists in connection with modern image-producing monitoring or controlling methods, such as computer tomography and nuclear spin tomography, since the magnetic field formed during application of these methods may cause the positioned clip to move, and such movement not only adversely affects the image quality, but it can also lead to a risk of the clip becoming loose. Furthermore, such clips produce image artefacts in nuclear spin tomography, which make it virtually impossible to judge the adjacent structures of the brain. Moreover, conventional clips cannot be applied in a stereotactical or endoscopical manner. The clips can then also only be used for open brain operations with relatively wide access openings, especially since the jaws of the pincer-like positioning tool considerably impairs direct inspection of the application region. The positioning tool, which can be found in WO 90/05491, can only be used in conjunction with clips having resilient properties. The flexible tubular probe of this positioning tool is then also proved to be unsuitable for the appropriate attachment of the clip, especially when a high degree of accuracy is crucial for the attachment of the clip, for example during manipulations in the region of the brain.

SUMMARY OF THE INVENTION

On the basis of this prior art, the basic requirement of the invention is a set for the treatment of vascular deformations, more especially for the treatment of deformations in the region of the brain, which overcomes the above-mentioned disadvantages.

The requirement is met by a set of such type for the treatment of vascular deformations, wherein the clamp (the clip), which is made from titanium, is formed by two semicirclar profiled bars, which are expanded in the relieved state and are brought together at the bottom end in a base, which is provided with corners on the periphery and is preceded by a clamping ring, which encloses the bars and is displaceable in the longitudinal direction of the clamp via a curved portion of the profiled bars, and a positioning bar, which is positionally secured relative to the handle, extends through the tubular probe, which is displaceable in the handle of the positioning tool in the axial direction relative to the handle and is resistant to bending.

A positioning tool, which has a rigid tubular probe, can already be found in U.S. Pat. No. 3,518,993 but, with this positioning tool, the tubular probe is secured relative to the handle and the positioning bar, which extends through the tubular probe, is displaceable relative to the tubular probe in the axial direction. A haemostatic clamp is also already described in DE-B-33 27 721, which is secured in the clamping position by a clamping ring, which is attached to said clamp, but this clamping ring is not incorporated into the clamp; rather, it is attached to the clamp, which is transferred into the clamping position, by means of an appropriately designed tool, such a mode of operation being unrealistic for manipulations, more especially in the region of the brain. A haemostatic clip, made from titanium, can be found in U.S. 5,201,746, but it is not in a configuration which permits it to be attached by means of a positioning tool, specifically in the region of the brain.

The use of titanium as a material for the clip takes account of the demand for absolute bio-compatibility and the demand for unlimited compatibility with computer tomography and nuclear spin tomography, but it requires a solution which differs from prior art and effects, on the one hand, the expansion of the arms of the clip, which is to be transferred into the application region, and, on the other hand, the bringing together of the arms of the clip which causes the attached clip to be clamped A detailed description both of the clip according to the invention and of the positioning tool according to the invention can be found in the description of the drawing. When a probe is used as the positioning tool, comparatively small access openings to the application region are advantageously required with an unhindered visual monitoring of the application region.

Appropriately configured component parts of the set are also, however, proved to be advantageous in conjunction with the fully orientated positioning of the clip. Furthermore, an embodiment of the positioning tool also proves expedient for the orientated positioning of the clip.

BRIEF DESCRIPTION OF THE DRAWINGS

The invention is explained more fully in the drawing with reference to schematically illustrated embodiments for the new clip and a positioning tool which comes into question therefor. In the drawing:

FIG. 3a is a front view of one of the arms of the clip;

FIGS. 1 and 2 are in a reduced, partially fragmented form, and FIGS. 3 to 8 are in an enlarged form.

DESCRIPTION OF THE PREFERRED EMBODIMENTS

Figure 1:
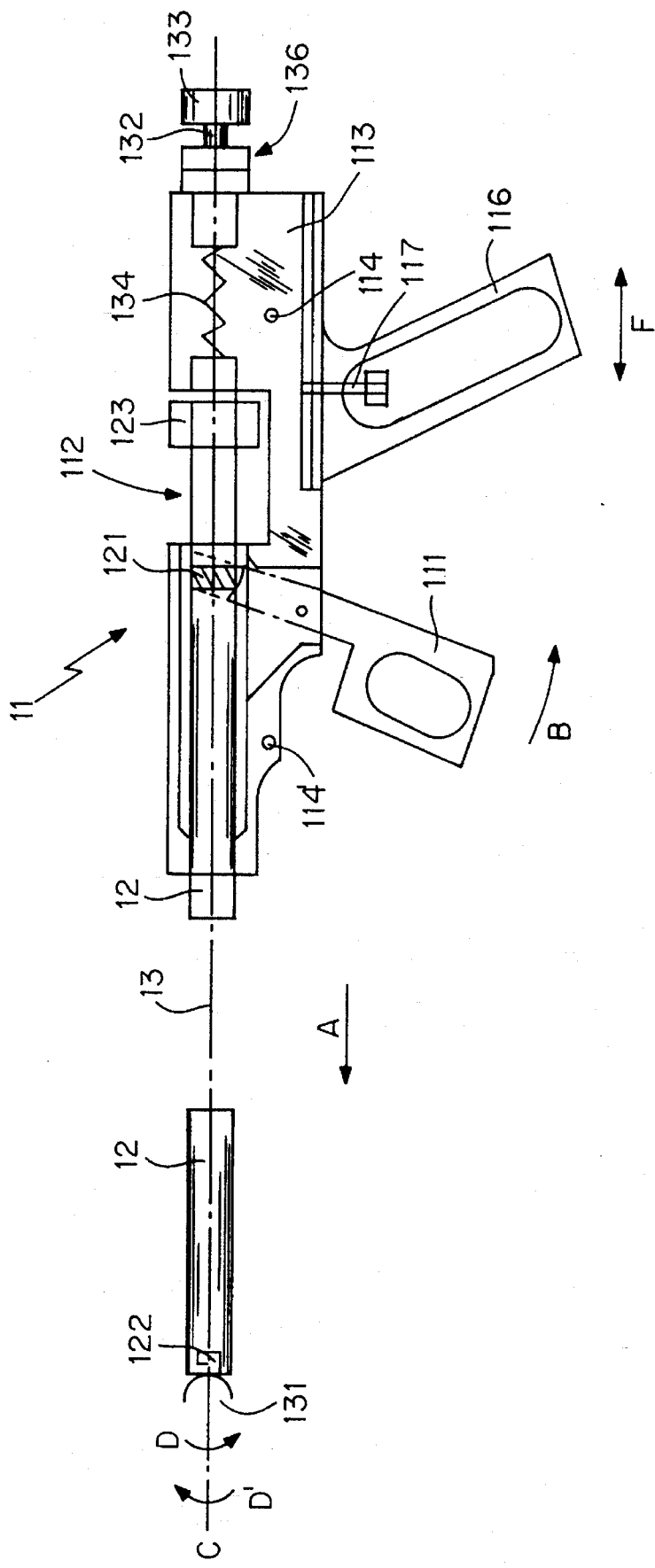
FIG. 1 is a side elevational view of the partially fragmented positioning tool, showing the tubular probe in its initial position.
Figure 2:
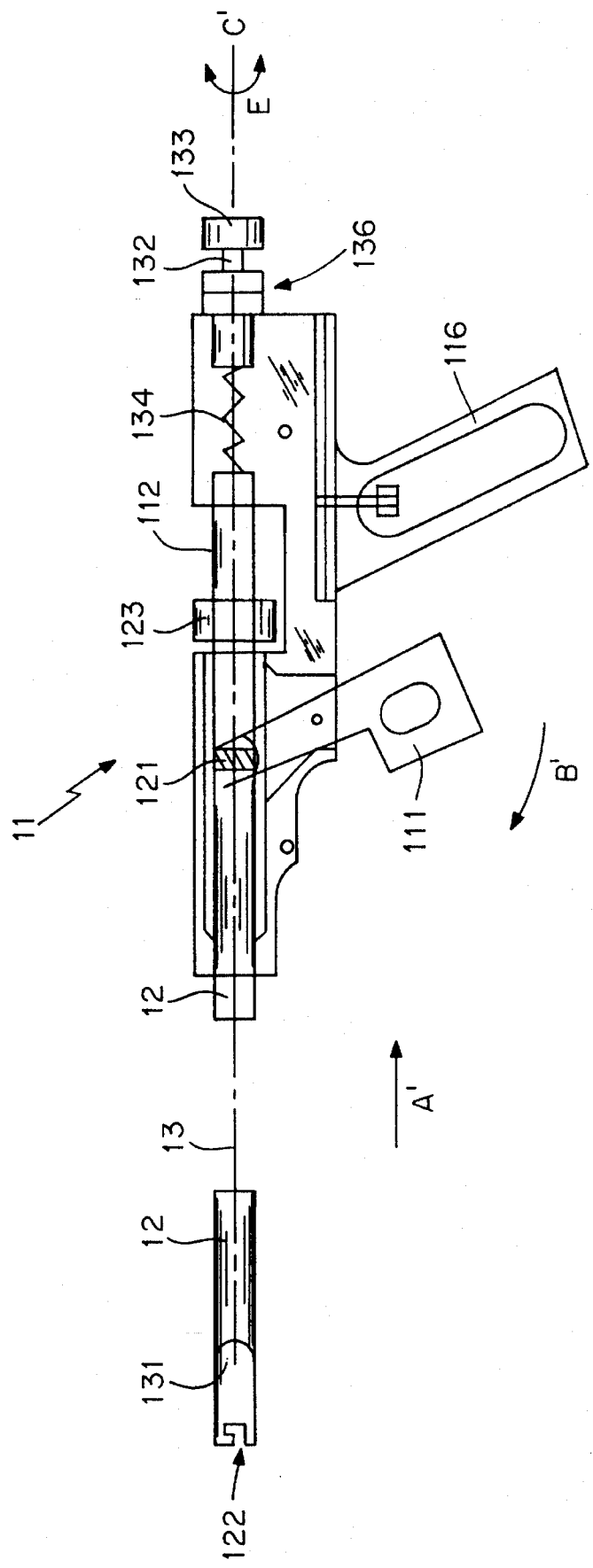
FIG. 2 illustrates the tool of FIG. 1 with the tubular probe in its other end position.

The positioning tool illustrated in FIGS. 1 and 2 comprises the tubular probe 12, which is incorporated into the handle 11 in the manner of the body of a pistol and is displaceable to a limited extent relative to the handle 11 in the direction of arrows A and A' in FIGS. 1 and 2 respectively by means of the operating clamp 111, which engages with an annular shoulder 121 of the tubular probe 12 and is pivotable in the direction of arrows B and B' in FIGS. 1 and 2 respectively. The positioning bar 13, is positionally secured relative to the handle 11 and hence the tubular probe 12, in the axial direction, is movable relative to the handle and relative to the positioning bar. the positioning bar 13 is provided on its free end with a positioning head 131, which is formed by claws 131', 131". . . , extends through the tubular probe 12, the claws 131', 131". . . of said positioning head being in the unclamped state, illustrated in FIG. 2, because of their resilient characteristic in the expanded position, from which they are transferable into the closed position illustrated in FIG. 1 through the tubular probe 12, which is displaceable over said claws. The tubular probe 12 then also has another receiving means 122, which extends from its end face, and, in conjunction therewith, in the region of the handle 11, namely in a recess 112 which exposes the tubular probe 12, an actuating ring 123 which is ridged on the periphery and by means of which the tubular probe 12 is rotatable about its longitudinal axis C in the direction of arrows D and D' respectively relative to the positioning bar 13. The positioning bar 13, which extends through the handle 11, is rotatable about its longitudinal axis C' in the direction of the double-headed arrow E in FIG. 2 together with the tubular probe 12 by means of an operating knob 133, which is attached to its projecting length 132 beyond the handle 11, after a block 136 has been raised which is caused by a spring 134. The handle 11 is easy to assemble and comprises two half-shells 113, which are brought together by screws 114 and 114'. The grip 116 of the handle 11 is associated with the handle so as to be displaceable for individual adaptability in the direction of the double-headed arrow F and so as to be securable on the handle (117). This tool serves to position, and then possibly also to release, the clip 21, which is described hereinafter and is illustrated in FIG. 3 in the unclamped state and in FIG. 8 in the clamped, that is to say attached, state, for the destruction of vascular deformities.

Figure 3:
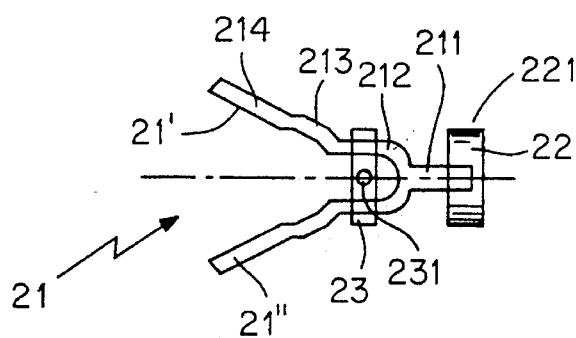
FIG. 3 is also a side elevational view of the new clip in its unclamped initial position.
Figure 4:
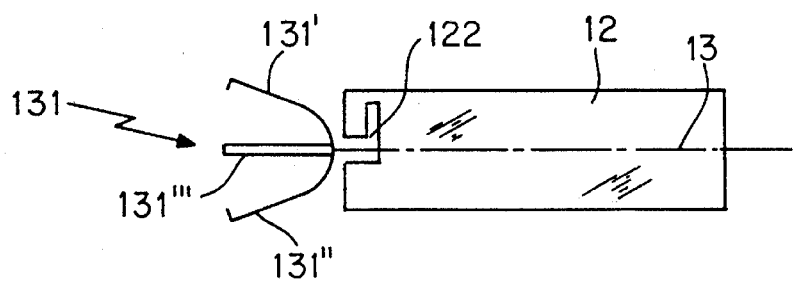
FIG. 4 illustrates the front end of the positioning tool on a larger scale.
Figure 5:
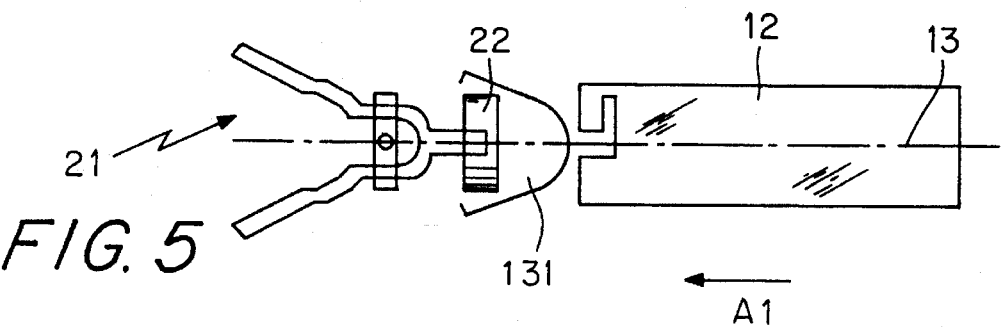
FIG. 5 illustrates the preliminary stage for the association of the clip of FIG. 2 with the tool.
Figure 6:
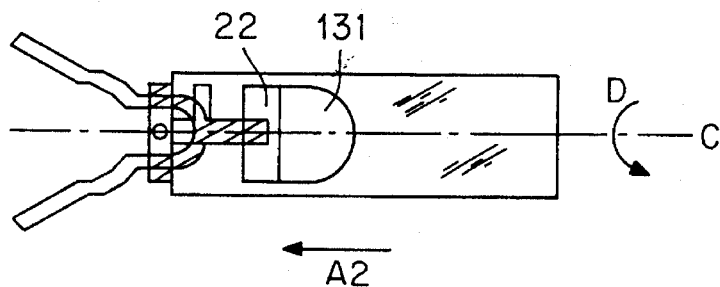
FIG. 6 illustrates an intermediate stage for the association of the clip with the tool.
Figure 7:
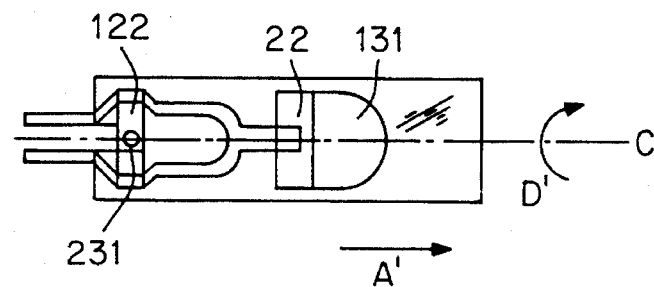
FIG. 7 illustrates the end stage for the association of the clip with the tool.
Figure 8:
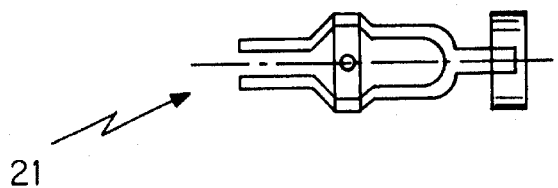
FIG. 8 illustrates the clip of FIG. 3 in its applied state.

The clip 21, which is to be applied by the positioning tool illustrated in FIGS. 1 and 2 and is illustrated in FIG. 3 in the unclamped state and in FIG. 8 in the positioned, that is to say clamped, state, comprises two arms 21' and 21" with the partial regions 211, 212, 213 and 214, of which the partial regions 211 at the bottom end are brought together so as to lie adjacent one another in a base 22 provided with corners 221. The outwardly offset region 212 communicates with the bottom end 211 of the arms 21' and 21" and extends into the curved portion 213, which communicates with the free end 214 of the arms 21' and 21" which is set back relative to the curved portion 213. A clamping ring 23, which surrounds the arms 21' and 21" of the clip 21, is associated with the clip 21 at the bottom end and surrounds, in its initial position (FIG. 3), the outwardly offset regions 212 of the arms 21' and 21" and displaces such in its clamping position illustrated in FIG. 7 over the curved portions 213 of the arms 21' and 21" which, in the positioned state of the clip 21, enclose a tissue region, which precedes the vascular deformations and is supplied with blood, and the clamping ring compresses the ends 214 of the arms 21' and 21" which sever vascular deformations in this manner. The clamping ring 23 is traversed by a mandrel 231 with a projecting length at both ends. The spacing between the regions 212 of the arms 21' and 21" of the clip 21, which is shown larger in the drawing, is so designed in natura that the mandrel 231, which traverses the clamping ring 23, supports or effects the expansion of the arms 21' and 21" as the clamping ring 23 transfers into the initial position illustrated in FIG. 3. Likewise, the set-back portion of the free ends 214 of the arms 21' and 21" of the clip 21 is so dimensioned that the ends of the arms in the clamped state are provided in natura with a substantially smaller spacing therebetween than is illustrated in FIG. 8. The unclamped clip (FIG. 3) is attached to the positioning tool, especially the head 131 of the positioning bar 13, when the tubular probe 12 is set-back relative to the positioning head (FIGS. 2 and 4) by the association of the base 22 of the clip 21 with the expanded claws 131', 131". . . of the positioning head 131 (FIG. 5). The tubular probe 12 is subsequently displaced in the direction of arrow A1 in FIG. 5 by tightening the actuating clamp 111 towards the hand grip 116 of the handle 11 in the direction of arrow B in FIG. 1, the tubular probe 12 being slipped over the positioning head 131 of the positioning bar 13 and pressing the initially expanded claws 131', 131". . . of the positioning head 131 towards the base 22 of the clip 21 so as to enclose the base 22 (FIG. 6). When the tubular probe 12 is displaced further in the direction of arrow A2 in FIG. 6, the mandrel 231 which traverses the clamping ring 23 associated with the clip 21 enters the receiving means 122 in the end face of the tubular probe 12. By subsequently rotating the tubular probe 12 in the direction of arrow D in FIGS. 1 and 6 relative to the positioning bar 13, the clamping ring 23 is secured in the receiving means 122 in the end face of the tubular probe 12 by means of the mandrel 231 traversing said ring. In the last described situation, which forms an intermediate stage between the situations shown in FIGS. 6 and 7, the clip 21 is transferred by the positioning tool through an opening extending into the interior of the body into the region in which the clip 21 is to be attached. In the appropriately attached state of the clip 21, the tubular probe 12 is then displaced further in the direction of arrow A2 in FIG. 6, whereby the clamping ring 23, which is secured relative to the tubular probe 12, is transferred from the initial position illustrated in FIG. 6 into the clamping position illustrated in FIG. 7, in which the clamping ring 23 compresses the ends 214 of the arms, which sever the vascular deformation, when slipped over the curved portions 213 of the arms 21' and 21" of the clip 21.

The actual positioning process is thereby terminated, and the positioning tool is removed from the positioned clip 21 after the release of the mandrel 231, which traverses the clamping ring 23, from the receiving means 122 in the end face of the tubular probe 12 by rotating the tubular probe 12 back relative to the positioning bar 13 in the direction of arrow D' in FIG. 7 and by subsequently displacing the tubular probe back in the direction of arrow A' in FIG. 7. The positioned clip 21 is basically illustrated in FIG. 8. In natura the clip is so configured that the ends 214 of the arms abut against one another in the positioned state so as to clampingly enclose the tissue region preceding the deformation to be destroyed.

If it proves necessary, for operative reasons, however, the situation shown in FIG. 7 can also already be produced in advance, and the clip, which is transferred into the application region in this situation, is then initially again transferred into an intermediate situation, prior to the actual attachment of the clip 21, the clip 21 being attached in said intermediate situation by arms 21' and 21" which are still expanded, and then being definitively applied.

As is apparent from FIG. 3a, the arms 21' and 21" of the clip 21 comprise a semicircular profile, the flat sides of which facing one another are advantageously roughened or ridged in the region of the ends 214 of the arms. Instead of an elongated configuration from the curved portions 213, the ends 214 of the arms may also assume an arcuate configuration or even, however, an angular configuration if the application region necessitates such.

If the clip 21 is only applied temporarily, the clip 21 is removed again from the application region with the positioning tool being appropriately operated in the opposite direction.

I claim:

1. Apparatus for treating vascular deformations, comprising: a clamp for closing a deformation; expanded arms on said clamp for attaching said clamp to said deformation, said clamp being formed of material compatible with the deformation; a positioning tool with a handle and an adjusting member; a tubular probe displaceable in said handle in an axial direction by said adjusting member; a positioning bar mounted in said handle and extending through said tubular probe and terminating in a gripper attachable to said clamp; said gripper having claws expandable out of engagement with said tubular probe when placed outside said tubular probe and displaced towards one another when said tubular probe is advanced and surrounds the claws for being enclosed by said tubular probe and being effective on said clamp; said clamp being of titanium, said arms being formed by two semicircular profiled bars expanded when in a relieved state; a base with corners on a periphery protruding laterally from the clamp, said semicircular profiled bars conveying together at a bottom end of said base, said semicircular profiled bars having a curved portion; a clamping ring enclosing said bars and being displaceable in a longitudinal direction of said clamp through said curved portion of said bars; said positioning bar being secured relative to said handle in an axial direction and extending through said tubular probe, said tubular probe being displaceable in said handle in an axial direction relative to said handle and being resistant to bending, said claws surrounding only said base and said corners of said base, said base limiting movement of said clamping ring in a backward direction, said claws engaging said base with the corners protruding from the clamp to hold the clamp during advancement of said tubular probe.

2. Apparatus as defined in claim 1, wherein said handle comprises a pistol body having a grip, said adjusting member for said tubular probe comprising a trigger guard.

3. Apparatus as defined in claim 2, wherein said tubular probe has an annular shoulder enclosed by a bifurcated end of said trigger guard.

4. Apparatus as defined in claim 1, wherein said tubular probe and said positioning bar are jointly securably mounted relative to said handle for being rotatable about a longitudinal axis of said probe.

5. Apparatus as defined in claim 1, wherein said handle has a securable hand grip displaceable in said longitudinal direction relative to bearing shells enclosing said tubular probe; and fastening means for bringing together said bearing shells.

6. Apparatus for treating vascular deformations, comprising: a clamp for closing a deformation; expanded arms on said clamp for attaching said clamp to said deformation, said clamp being formed of material compatible with the deformation; a positioning tool with a handle and an adjusting member; a tubular probe displaceable in said handle in an axial direction by said adjusting member; a positioning bar mounted in said handle and extending through said tubular probe and terminating in a gripper attachable to said clamp; said gripper having claws expandable out of engagement with said tubular probe when placed outside said tubular probe and displaced towards one another when said tubular probe is advanced and surrounds the claws for being enclosed by said tubular probe and being effective on said clamp; said clamp being of titanium, said arms being formed by two semicircular profiled bars expanded when in a relieved state; a base with corners on a periphery protruding from the clamp, said semicircular profiled bars conveying together at a bottom end of said base, said semicircular profiled bars having a curved portion; a clamping ring enclosing said bars and being displaceable in a longitudinal direction of said clamp through said curved portion of said bars; said positioning bar being secured relative to said handle in an axial direction and extending through said tubular probe, said tubular probe being displaceable in said handle in an axial direction relative to said handle and being resistant to bending, said tubular probe having an end face with receiving means; a mandrel for traversing said clamping ring and received in said receiving means; said mandrel protruding at two ends beyond said semicircular profiled bars; said receiving means comprising a bayonet-type securing means; said tube being mounted in said handle for being rotatable about a longitudinal axis of said tube.

7. Apparatus as defined in claim 6, wherein said handle has a recess exposing said tubular probe, said adjusting member being associated with said tubular probe in a region of said recess for rotating said tubular probe relative to said positioning bar.

8. Apparatus as defined in claim 7, wherein said adjusting member comprises a knurled ring associated with said tubular probe.

9. Apparatus for treating vascular deformations, comprising: a clamp for closing a deformation; expanded arms on said clamp for attaching said clamp to said deformation, said clamp being formed of material compatible with the deformation; a positioning tool with a handle and an adjusting member; a tubular probe displaceable in said handle in an axial direction by said adjusting member; a positioning bar mounted in said handle and extending through said tubular probe and terminating in a gripper attachable to said clamp; said gripper having claws expandable out of engagement with said tubular probe when placed outside said tubular probe and displaced towards one another when said tubular probe is advanced and surrounds the claws for being enclosed by said tubular probe and being effective on said clamp; said clamp being of titanium, said arms being formed by two semicircular profiled bars expanded when in a relieved state; a base with corners on a periphery protruding from the clamp, said semicircular profiled bars conveying together at a bottom end of said base, said semicircular profiled bars having a curved portion; a clamping ring enclosing said bars and being displaceable in a longitudinal direction of said clamp through said curved portion of said bars; said positioning bar being secured relative to said handle in an axial direction and extending through said tubular probe, said tubular probe being displaceable in said handle in an axial direction relative to said handle and being resistant to bending, said tubular probe and said positioning bar being jointly securably mounted relative to said handle for being rotatable about a longitudinal axis of said probe; including a spring-and-block mounting of said tubular probe rlative to said handle.

* * * * *